(12) United States Patent
Heinemann (10) Patent No.: US 8,556,899 B2
(45) Date of Patent: Oct. 15, 2013

(54) SURGICAL INSTRUMENT

(76) Inventor: Norbert Heinemann, Spaichingen (DE)

( * ) Notice: Subject to any disclaimer, the term of this patent is extended or adjusted under 35 U.S.C. 154(b) by 311 days.

(21) Appl. No.: 12/832,577

(22) Filed: Jul. 8, 2010

(65) Prior Publication Data

US 2012/0010622 A1    Jan. 12, 2012

(51) Int. Cl.
*A61B 17/32* (2006.01)

(52) U.S. Cl.
USPC .............................. 606/83; 606/167; 606/205

(58) Field of Classification Search
USPC ......... 606/79, 83–84, 90, 110, 167–168, 170, 606/172, 174, 184, 205–210, 99, 246; 600/104–105, 141, 210, 213–214, 600/562–572; 227/175.1–175.4, 176.1; 81/126, 128–129, 381; 42/90, 95
See application file for complete search history.

(56) References Cited

U.S. PATENT DOCUMENTS

| | | | | |
|---|---|---|---|---|
| 606,078 A | * | 6/1898 | Pattberg | 606/110 |
| 1,299,928 A | | 4/1919 | Ermold | |
| 1,347,651 A | * | 7/1920 | Nauth | 606/112 |
| 4,043,343 A | * | 8/1977 | Williams | 606/207 |
| 5,584,844 A | * | 12/1996 | Weisshaupt | 606/170 |
| 5,961,531 A | | 10/1999 | Weber et al. | |
| 6,261,294 B1 | * | 7/2001 | Stihl et al. | 606/83 |
| 2004/0044346 A1 | | 3/2004 | Boury | |
| 2006/0189995 A1 | * | 8/2006 | Lancial | 606/83 |

FOREIGN PATENT DOCUMENTS

| | | |
|---|---|---|
| DE | 83001 | 9/1895 |
| DE | 43 16 768 | 11/1994 |
| DE | 197 02 079 | 7/1998 |
| DE | 299 24 518 | 7/2003 |
| DE | 10 2006 043 970 | 4/2008 |

* cited by examiner

*Primary Examiner* — Todd Manahan
*Assistant Examiner* — Eric Gibson
(74) *Attorney, Agent, or Firm* — Lucas & Mercanti, LLP; Klaus P. Stoffel (57) ABSTRACT

A surgical instrument, in particular a laminectomy rongeur or a conchotome, with a shaft and with a one-piece sliding part, longitudinally displaceable relative to the shaft, with which for longitudinal displacement a grip part is associated which is pivotable about a pivot axis, wherein the sliding part is able to be transferred from a working position, in which the sliding part is guided longitudinally displaceably on the shaft in a guide, into a cleaning position, in which the sliding part is freed from the guide and is pivotable relative the shaft about a rotation axis oriented perpendicularly to the longitudinal extent of the shaft. The rotation axis is aligned perpendicularly to the pivot axis of the pivotable grip part.

16 Claims, 5 Drawing Sheets

SURGICAL INSTRUMENT

BACKGROUND OF THE INVENTION

The invention relates to a surgical instrument, in particular a laminectomy rongeur or a conchotome.

Such surgical instruments, also designated as sliding shaft instruments, are sufficiently known. Generally, laminectomy rongeurs are used as a punch for cutting through tissue, cartilage or bone and are used in particular in spinal operations. Sliding shaft instruments are distinguished by a sliding part, longitudinally displaceable relative to a fixed shaft, which sliding part is displaceable by actuation of a pivotable grip part (gripping arm) in the direction of the longitudinal extent of the shaft. Usually, the sliding part and the shaft cooperate here with distal working ends in the manner of a punch.

A problem in known surgical instruments is mostly their only inadequate and complex cleanability. In order to be able to clean sliding shaft instruments in an improved manner, in particular in a region between the sliding part and the shaft, into which biological material can enter during the operation, sliding shaft instruments have become known, in which the sliding part is to be arranged fully or partially so as to be pivotable about a rotation axis running transversely to the longitudinal extent of the shaft and parallel to the pivot axis of the grip part, in order to hereby optimize the accessibility of a sliding part guide for cleaning purposes. Sliding shaft instruments with a sliding part pivotable about a rotation axis are described for example in DE 10 2006 043 970 A1, DE 299 24 518 U1 or U.S. Pat. No. 5,961,531 A. A disadvantage in the known surgical instruments is that the sliding part is not able to be transferred by single-handed operation from a working position into a cleaning position, in which it is pivotable about the rotation axis. An additional disadvantage is that known surgical instruments to some extent have to be dismantled for cleaning purposes. i.e. the sliding part has to be removed from the shaft part after pivoting about the rotation axis.

In addition to the previously described laminectomy rongeurs, sliding shaft instruments constructed as a conchotome are known, which inter alia are used as intervertebral disc forceps or also in operations for the reduction of nasal conchae. As in the case of laminectomy rongeurs, the problem of an only insufficient cleanability also exists with conchotomes.

SUMMARY OF THE INVENTION

The invention is based on the problem of indicating an alternative, readily cleanable sliding shaft instrument. The sliding part is preferably to be able to be transferred into a cleaning position by single-handed operation. It is further preferable that the surgical instrument is to be distinguished by a simple construction.

This problem is solved by a surgical instrument (sliding shaft instrument) with the features of Claim 1. Advantageous further developments of the invention are indicated in the sub-claims. All combinations of at least two of the features disclosed in the description, the claims and/or the figures, fall within the framework of the invention.

The invention has identified that it is necessary as a prerequisite to solve all the above-mentioned problems to depart from the hitherto usual construction and not to arrange the rotation axis, about which the (single) one-piece sliding part is pivotable in its cleaning position, as in the prior art simultaneously perpendicularly to the longitudinal extent of the shaft and perpendicularly to the longitudinal extent of the pivotable grip part, but rather such that the sliding part is pivotable in a rotation plane which runs perpendicularly to a plane spanned from the shaft part and the pivotable grip part. In other words, the rotation axis about which the sliding part of a surgical instrument according to the invention is pivotable in its cleaning position, does not run as in the prior art parallel to the pivot axis about which the pivotable grip part is pivotable on actuation, but rather lies in an imaginary plane spanned from the grip part and the shaft part, i.e. therefore runs both perpendicularly to the longitudinal extent of the shaft part and also perpendicularly to the pivot axis of the pivotable grip part. This totally new manner of construction guarantees for the first time a simple and readily cleanable construction of the surgical instrument and surprisingly makes possible, by additional measures which are to be further explained later, a single-handed transferability of the sliding part from the working position into its cleaning position. Preferably, the single-piece sliding part, viewed from the rotation axis, extends in two opposite directions, preferably in each of the two directions with a length of at least 1 cm, preferably of at least 2 cm, still further preferably of at least 3 cm.

An embodiment of the surgical instrument is quite particularly preferred in which the sliding part does not have to be removed from the shaft for cleaning the upper side of the shaft and the underside of the sliding part, but rather is also held undetachably on the shaft after the pivoting about the rotation axis. Hereby, the necessity frequently occurring in the prior art for the re-assembly of the surgical instrument after a cleaning process is dispensed with. In order to hold the sliding part undetachably on the shaft part, it is possible to form the rotation axis by means of a threaded pin or rivet pin, which is held (caught) in a counter-element.

In a further development of the invention, provision is advantageously made that locking means are provided for the sliding part, which secure the sliding part in the working position in which it is arranged so as not to be pivotable about the rotation axis, but so as to be guided longitudinally displaceably relative to the shaft, in order to reliably prevent an unintended transfer into the cleaning position, in which the sliding part is then pivotable about the rotation axis relative to the shaft.

The locking means are quite particularly preferably constructed such that on actuation they are constructed displacing a stop position for the pivotable grip part, mechanically coupled (operatively connected) with the sliding part. Here, the different stop positions on the one hand define the working position, in which the sliding part is guided as to be non-rotatable longitudinally displaceably on the shaft part and on the other hand the cleaning position, in which the sliding part is freed from the guide and is pivotable about the rotation axis relative to the shaft. In other words, the locking means makes possible, after actuation, a further pivoting of the grip part compared with the working position, and hence a further longitudinal displacement of the sliding part relative to the shaft (preferably toward the rear), so that the sliding part comes free from the guide and is then pivotable in the cleaning position about the rotation axis.

An embodiment of the surgical instrument is quite particularly preferred, in which the different stop positions for the pivotable grip part are formed by different diameter sections of a locking bolt of the locking means, wherein the diameter sections differ as regards the size of their diameter. Preferably, the diameter section defining the cleaning position has a smaller diameter than the diameter section defining the working position, in order to thereby make possible a further pivoting of the pivotable grip part and hence a further longitudinal displacement of the sliding part relative to the shaft part.

It is particularly expedient if the previously mentioned locking bolt, having at least two different diameter sections, is spring-loaded, preferably such that the locking bolt is displaceable contrary to the force of the spring into the unlocking or respectively unblocking position defining the cleaning position. The spring therefore strives to block the locking means automatically and to secure the sliding part in its working position.

The provision of locking means with a locking bolt having at least two, in particular axially adjacent diameter sections makes possible, in combination with the alignment according to the invention of the rotation axis for the sliding part, a good single-handed operability of the surgical instrument.

An embodiment of the surgical instrument is quite particularly preferred in which the pivotable grip part is spring-loaded against the locking bolt, having at least two diameter sections, of the locking means, i.e. in the direction of its stop position, so that the pivotable grip part and hence the sliding part, after actuation of the locking bolt, is immediately automatically displaced into the cleaning position, in which the sliding part is pivotable about the rotation axis relative to the shaft. Such an embodiment is optimal with regard to ensuring single-handed operability.

It is particularly expedient if for the spring-loading of the pivotable grip part, an—in particular two-part—expander spring is provided, which is arranged between the pivotable grip part and a grip part which is preferably constructed in one piece with the shaft, wherein it is further preferred if the expander spring is arranged resting on both aforementioned grip parts and strives to press the grip parts apart and hence to pivot the pivotable grip part about the pivot axis running perpendicularly to the rotation axis of the sliding part.

As already previously indicated, it is particularly preferred if the locking bolt of the locking means is able to be transferred, contrary to the elastic force of a spring, from its securing position, in which the locking bolt secures the sliding part in its working position, into a release position (unblocking position, unlocking position), in which the sliding part is pivotable about the rotation axis, wherein the stop position for the pivotable grip part in the release position is displaced with respect to the stop position for the pivotable grip part in the securing position, preferably in proximal direction, i.e. in a direction away from the distal working ends of sliding part and shaft.

As already explained in the introduction, it is particularly preferred if the surgical instrument is constructed as a rongeur operating in the manner of a punch, by means of which great forces can be applied in the region of the distal working ends of shaft and sliding part, in order to be able to cut through in particular tissue, cartilage and/or bone. Preferably the shaft and sliding part cooperate for this in the region of their distal working ends in the manner of a punch.

In addition to an embodiment in which the shaft and the sliding part cooperate directly with their digital working ends, in particular in the manner of a punch, ah embodiment is able to be realized in which a pivotably arranged acting member part (in particular jaw part) is able to be actuated by the sliding part. The acting member (in particular jaw) of the surgical instrument preferably acts here in the manner of a scissors or forceps. An embodiment of the surgical instrument as a conchotome is quite particularly preferred, in particular for use as an intervertebral disc forceps or in ear, nose and throat operations, wherein a conchotome Is distinguished by a forceps-like jaw with at least one, preferably exclusively one, pivotably arranged jaw part.

The sliding part for actuating the jaw part is preferably in engagement with the jaw part at a distance from a pivot axis of the jaw part. In other words, the sliding part is coupled articulately with the jaw part for the pivoting thereof about the pivot axis at a distance from the pivot axis of the jaw part.

There are various possibilities with regard to the actual construction of the coupling of the sliding part with the jaw part. Thus, it is able to be realized for example that the sliding part is not mechanically coupled with the jaw part directly, but rather indirectly via at least one intermediate part. Quite particularly preferable, however, is a direct coupling of sliding part and jaw part, preferably such that a receiving slot, preferably open on the end side, is realized on the jaw part, into which the sliding part engages with a preferably bar- or rod-shaped carrier section. By longitudinal displacement of the sliding part, the jaw part is then pivoted about its pivot axis, wherein with this pivot movement also the jaw part is pivoted relative to the sliding part. The receiving slot is advantageously arranged and shaped here such that this relative displacement movement between jaw part and sliding part becomes possible. Quite particularly preferably, the receiving slot does not run in a straight line, but rather is contoured so as to be oblique or curved, wherein it is still further preferred if the receiving slot (somewhat towards the front) with the jaw closed is bent towards the distal end of the surgical instrument.

An embodiment of the surgical instrument, in particular of the conchotome, is particularly preferred in which the receiving slot is constructed facilitating a dismantling of the surgical instrument for cleaning purposes. The receiving slot is preferably constructed for this such that when the locking arrangement of the surgical instrument is unlocked and the jaw part is actuated directly manually, the carrier section of the sliding part is displaced out from the receiving slot, in order to be able to thereafter pivot about the rotation axis for cleaning purposes. The receiving slot is preferably contoured in a curved form for this in the manner of a guide link.

In particular, in a realized embodiment of the receiving slot as previously described, it is preferred if the carrier section, in particular in the shape of a bar or rod, is supported at both end sides, by the carrier section being received between two side sections of the sliding shaft. The carrier section is preferably constructed in one piece with the two side sections of the sliding shaft, wherein it is alternatively able to be realized to construct the carrier section as a separate component and to secure it between the side sections of the sliding shaft, for example by welding or accommodation in two fixing openings. In an alternative embodiment, the carrier section is only fixed on one side and has a free end. In such an embodiment, the carrier section can simply be guided out from the receiving slot of the jaw part by lateral pivoting of the sliding part. Such an embodiment is suitable in particular for comparatively large surgical instruments, in which the carrier section has a sufficient thickness extent for reasons of stability.

There are various possibilities with regard to the embodiment of the guide, which guides the sliding part along the shaft on actuation of the pivotable grip part. An embodiment of the guide is particularly preferred as a T-slot in cross-section, preferably provided in the shaft and open at the top. Particularly preferably, the sliding part engages into the T-slot with a guide extension shaped correspondingly in a T-shape in cross-section, wherein the sliding shaft can come free from the T-slot, in particular upwards, when the locking means are unlocked, i.e. are in the release position, and otherwise is caught axially displaceably in the guide.

Basically, an embodiment is able to be realized, in which the sliding part can come free directly laterally out of the guide with the (unlocked) locking means situated in the release position, wherein for this preferably a lateral recess is realized in the shaft. An embodiment is particularly preferred, however, in particular with the construction of the surgical instrument as a conchotome, in which the sliding part, preferably by internal stress, is pre-stressed in a direction away from the shaft, so that the sliding part, with the locking means unlocked and with an uncoupling from the jaw part, automatically displaces itself into a position in which it is pivotable about the rotation axis. Particularly preferably, the sliding part for realizing the internal stress is shaped so as to be (slightly) curved and deforms elastically in a guided state in the guide, so that the sliding part, as long as it is guided longitudinally displaceably, is pre-stressed, in order to then, with the locking means unlocked, pivot or respectively give away from the shaft, preferably in the direction of the longitudinal extent of the rotation axis away from the shaft, i.e. preferably upwards, to then be pivoted about the rotation axis.

The invention also leads to a surgical instrument, disclosed and able to be claimed as an independent invention, which is distinguished by optimized locking means which secure the sliding part against an unintended transfer into the cleaning position. These locking means were previously already described in connection with a rotation axis running perpendicularly to the pivot axis of the pivotable grip part, wherein the locking means, constructed according to the concept of the invention, are also able to be realized with differently oriented rotation axes for the sliding part, for example running parallel to the pivot axis. The locking means are distinguished in that they form a stop for the pivotable grip part of the surgical instrument, wherein two different diameter sections of a locking bolt of the locking means define two different stop positions for the pivotable grip part, wherein one of the stop positions defines the working position and the other stop position defines the cleaning position of the longitudinally displaceable sliding part, pivotable about the rotation axis. An embodiment of the surgical instrument is quite particularly preferred in which the pivotable grip part is acted upon by elastic force against the locking bolt of the locking means.

The invention therefore relates to a surgical instrument, in particular a laminectomy rongeur or a conchotome, in particular according to one of the preceding claims, with a shaft and with a sliding part longitudinally displaceable relative to the shaft, with which a grip part, pivotable about a pivot axis, is associated for the longitudinal displacement, wherein the sliding part is able to be transferred from a working position, in which the sliding part is guided longitudinally displaceably on the shaft in a guide, into a cleaning position, in which the sliding part is freed from the guide and is pivotable relative to the shaft about a rotation axis oriented perpendicularly to the longitudinal extent of the shaft, wherein locking means are provided with which the sliding part is able to be secured in the working position against an unintended transfer into the cleaning position, wherein the locking means has a locking bolt, displaceable preferably perpendicularly to the rotation axis, with a first diameter section defining the stop position for the pivotable grip part in the working position, and a second diameter section defining the stop position for the pivotable grip part in the cleaning position. In a further development of the invention, provision is advantageously made that the locking means are constructed displacing a stop position for the pivotable grip part. In a further development of the invention, provision is advantageously made that the diameter of the first diameter section is greater than the diameter of the second diameter section. In a further development of the invention, provision is advantageously made that the pivotable grip part is spring-loaded against the locking bolt.

Further advantages, features and details of the invention will be apparent from the following description of preferred example embodiments and with the aid of the drawings.

BRIEF DESCRIPTION OF THE DRAWINGS

These show in:

FIG. 10b: an enlarged illustration of the opened jaw of FIG. 10a, FIG. 11a: a surgical instrument constructed as a conchotome with closed jaw, FIG. 11b: an enlarged illustration of the closed jaw of FIG. 11a, and FIG. 12: a top view onto a surgical instrument constructed as a conchotome with a sliding part pivoted about a rotation axis running in vertical direction.

DETAILED DESCRIPTION OF THE INVENTION

In the figures, the same elements and elements with the same function are marked by the same reference numbers.

Figure 1:
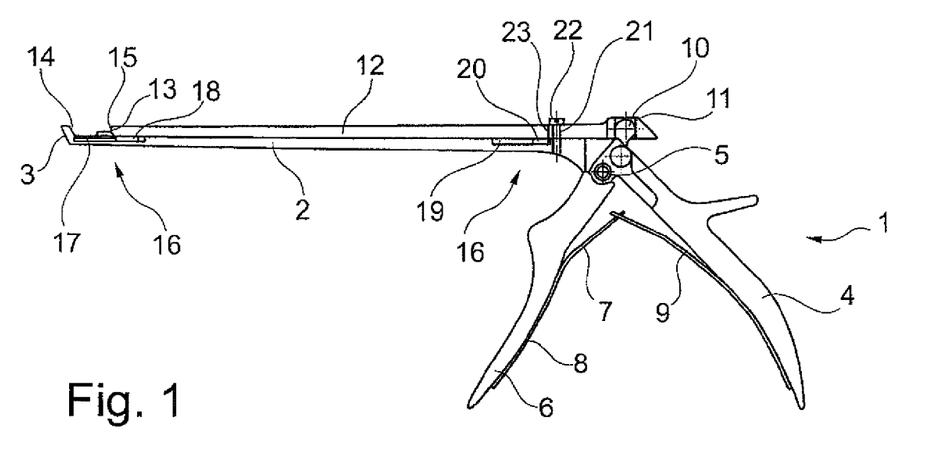
FIG. 1: a side view (partially in section) of a surgical instrument constructed as a sliding shaft instrument, wherein the sliding part is in a working position in which the sliding part is guided longitudinally displaceably to the shaft.
Figures 2, 3:
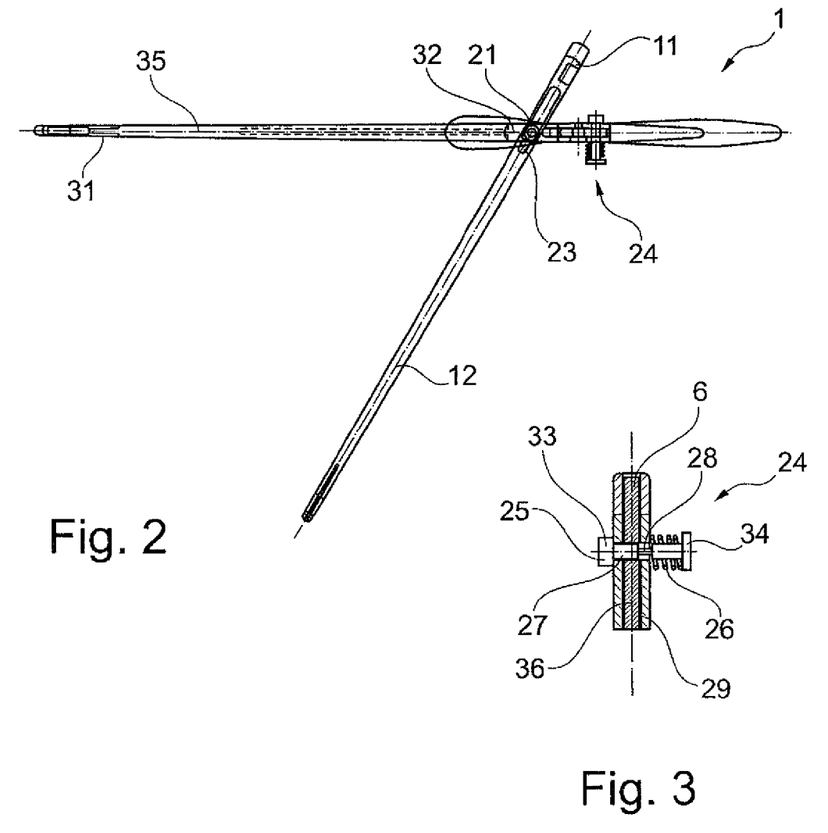
FIG. 2: a top view onto the surgical instrument according to FIG. 1, wherein the sliding part is in a cleaning position, in which the sliding part (as shown) is pivotable about a rotation axis relative to the shaft, wherein the rotation axis extends both perpendicularly to the longitudinal extent of the shaft and also perpendicularly to a pivot axis, which is a front, pivotable grip part of the surgical instrument.
FIG. 3: shows an enlarged detail illustration, partially in section, of locking means to secure the sliding part in its working position.

In FIGS. 1 and 2 a surgical instrument 1 is shown, serving as a punch. The surgical instrument 1 comprises an elongated shaft 2 with a distal (front) working end 3. A rear grip part 4 (gripping arm) is constructed in one piece with the shaft 2.

Relative to the fixed, proximal (rear) grip part 4, a distal (front) pivotable grip part 6 is pivotably arranged about a pivot axis 5 running transversely to the longitudinal extent of the shaft 2. Between the two grip parts 4, 6 an expander spring 7 is arranged in a manner known per se, which in the example embodiment shown is formed from two plate spring parts 9, wherein each plate spring part 8, 9 is screwed with a grip part 6, 4, and wherein the plate spring parts 8, 9 engage into each other with their free ends.

The pivotable (front) grip part 6 has an upper, approximately ball-head shaped end 10, which engages into a laterally open recess 11 of a one-piece sliding part 12. In this way, the sliding part 12 is longitudinally displaceable relative to the shaft 2 about the pivot axis 5 by means of the front, pivotable grip part 6, by pivoting thereof.

The sliding part 12 has a distal (front) working end 13, which cooperates with the front working end 3 of the shaft 2 in the manner of a punch. For this, the working ends 3, 13 have cutting surfaces 14, 15 (punch surfaces) facing each other.

In FIG. 1 the sliding part 12 is shown in a working position. In the working position, the sliding part 12 is guided longitudinally displaceably on the shaft 2. A guide track 17, into which a lower guide extension 18 engages in the region of the distal end region of the sliding part 12, is provided as guide 16 in the region of the distal end region of the shaft 2. In addition, the guide 16 comprises, in a region at a distance proximally to the working ends 3, 13, a guide track 19 on the shaft 2, which likewise cooperates with a lower guide extension 20 of the sliding part 12. The guide 16 is designed so that the sliding part 12 is caught in the guide 16 in its working position over the entire longitudinal displacement path along the shaft, i.e. also in a distally deflected and in a proximally deflected end position.

In order to make possible a facilitated cleaning of the surgical instrument 1, a rotation axis 21 is provided for the sliding part 12, about which the entire one-piece sliding part 12 is displaceable. The sliding part extends in two opposite radial directions, starting from the rotation axis. A pivoting about this rotation axis 21 is, however, not possible in the shown working position, in which the sliding part 12 is caught in the guide 16. As can be seen from FIG. 1, an elongated hole 23 in the sliding part 12 penetrates the rotation axis 21 formed by a head screw 22, so that the sliding part 12 is longitudinally displaceable relative to the rotation axis 21. The head screw 22 further penetrates the shaft 2 and, as will be further explained later, is held (caught) in a counter-element (cf. FIG. 7).

Locking means 24, illustrated in FIG. 3, are associated with the sliding part 12, which secure the sliding part 12 in the working position illustrated in FIG. 1. The locking means 24 comprise a locking bolt 25, which contrary to the force of a spring 26, constructed as a helical compression spring, is displaceable from the securing position defining the working position illustrated in FIG. 3 into a release position (unlocking, unblocking position). The locking bolt 25 comprises a cylindrical, first diameter section 27, which defines a first stop position for the pivotable grip part 6. Axially adjoining the first diameter section 27 is a second diameter section 28, produced by turning, which defines a stop position for the pivotable grip part 6 in a cleaning position of the sliding part 12. In other words, the second diameter section 28 defines a stop for the pivotable grip part 6, which in turn defines the cleaning position of the sliding part 12, in which the sliding part 12 is pivotable about the rotation axis 21. As can be seen from FIG. 3, the locking bolt 25, oriented parallel to the pivot axis 5 and perpendicularly to the rotation axis 21, penetrates the component formed from the shaft 2 and the proximal grip part 4. In so doing, the locking bolt 25 projects through an inner recess 29, in which a section 30 of the pivotable grip part 6 is held. The locking bolt 25 is held undetachably. For this, the locking bolt 25 has radially widened ends 33, 34, which reliably prevent a pushing out of the locking bolt 25 from the through-opening receiving it.

Figure 8:
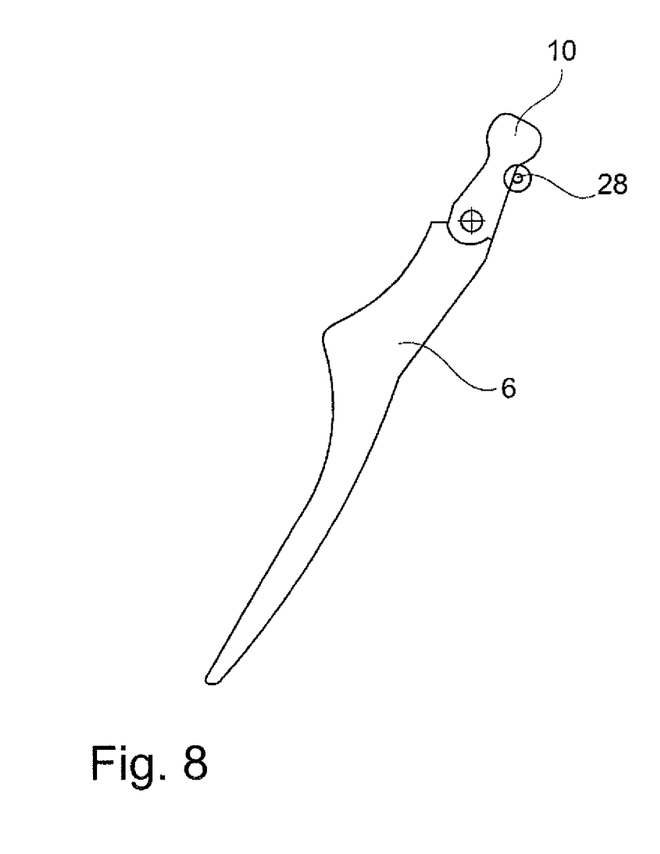
FIG. 8: an illustration of the pivotable grip part in its unlocked position, in which the sliding part is transferred into the cleaning position.
Figure 9:
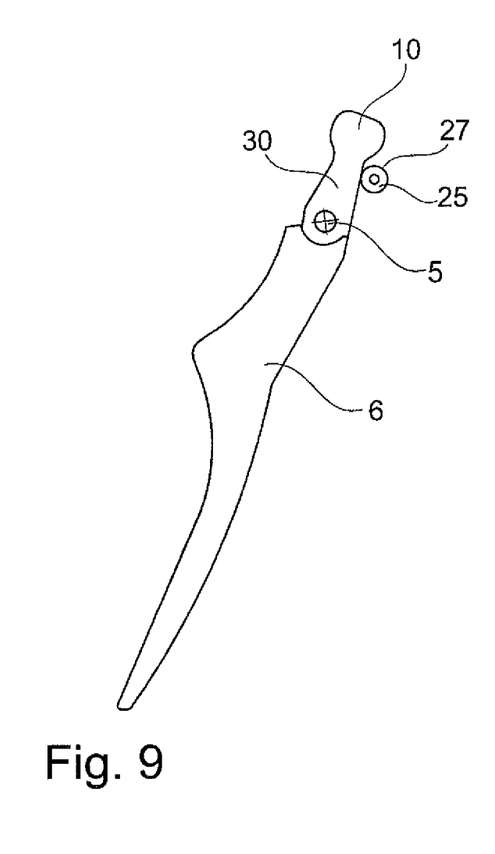
FIG. 9: an illustration of the pivotable grip part in its securing position, in which the sliding part is secured against unintended transfer into the cleaning position.

The locking means 24 can be seen particularly well from a review of FIGS. 3, 8 and 9 together.

As explained, in FIG. 3 a securing position of the locking bolt 25 is shown. This can also be seen in FIG. 9. It can be seen that the pivotable grip part 6 lies against the first diameter section 27, i.e. a stop position for the pivotable grip part 6 lies relatively far distally. For the proximal displacement of the stop position for the pivotable grip part 6, the locking bolt 25 is actuated contrary to the elastic force of the spring 26, so that the second, reduced diameter section 28 comes to lie in the region within the inner recess 29 and the pivotable grip part 6 cooperates with the second diameter section 28. In this release position, the stop position for the pivotable grip part 6 is displaced in proximal direction, so that the sliding part 12, which is coupled via the upper end 10 with the pivotable grip part 6, can be displaced further towards the rear, i.e. proximally. In this position, displaced towards the rear (cleaning position), the sliding part 12 is free from the guide 16, i.e. the guide extension 18 is no longer in engagement with the guide track 17, and the guide extension 20 is no longer in engagement with the guide track 19, but rather the guide extensions 18, 20 can be pivoted out through lateral recesses 31, 32. Through the fact that in the release position the sliding part 12 is no longer caught in the guide 16, the sliding part 12 can be pivoted about the rotation axis 21, i.e. in a horizontal plane.

An optimum single-handed operability of the surgical instrument 1 or respectively of the locking means 24 is therefore provided, because the pivotable grip part 6 is acted upon by elastic force via the expander spring 7 always in the direction of the respective stop position, i.e. in the direction of the locking bolt 25, so that the pivotable grip part 6 pivots automatically after actuation of the locking bolt 25 with its upper region proximally, i.e. towards the rear and therefore snaps into the release position, which at the same time defines the cleaning position of the sliding part 12.

FIG. 2 shows the surgical instrument 1 with sliding part 12 pivoted in the cleaning position. It can be seen that in this pivoted state, a shaft upper side 35, which is otherwise concealed by the sliding part 12, is able to be optimally cleaned. The same applies to a shaft underside, facing the shaft upper side 35, which can not be seen in FIG. 2.

In FIGS. 4 to 7, various individual parts of the surgical instrument 1 are illustrated, wherein here it is again to be noted that the surgical instrument 1 in practice does not have to be dismantled into these individual parts, but rather is able to be cleaned optimally in the assembled state.

Figure 4:
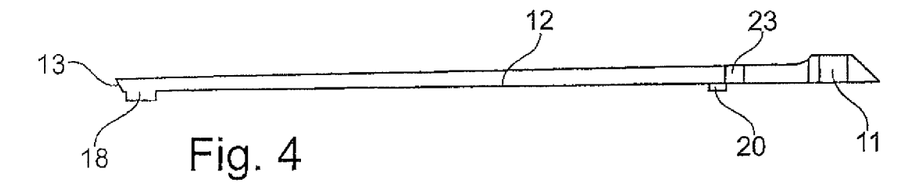
FIG. 4: a dismantled sliding part.

The elongated sliding part 12 can be seen in FIG. 4, with its distal lower extension 18 and with its proximal lower guide extension 20, wherein the guide extensions 18, 20 are part of the guide 16. In addition, the elongated hole 23 can be seen, which is usually penetrated by the head screw 22 (cf. FIG. 7), and which ensures a relative displacement of the sliding part 12 relative to the rotation axis 21. Furthermore, the distal working end 13 can be seen, and the laterally open recess 11 situated in the proximal region, which makes possible an uncoupling of the sliding part 12 from the pivotable grip part 6 by pivoting of the sliding part 12 about the rotation axis 21.

Figures 5, 6, 7:
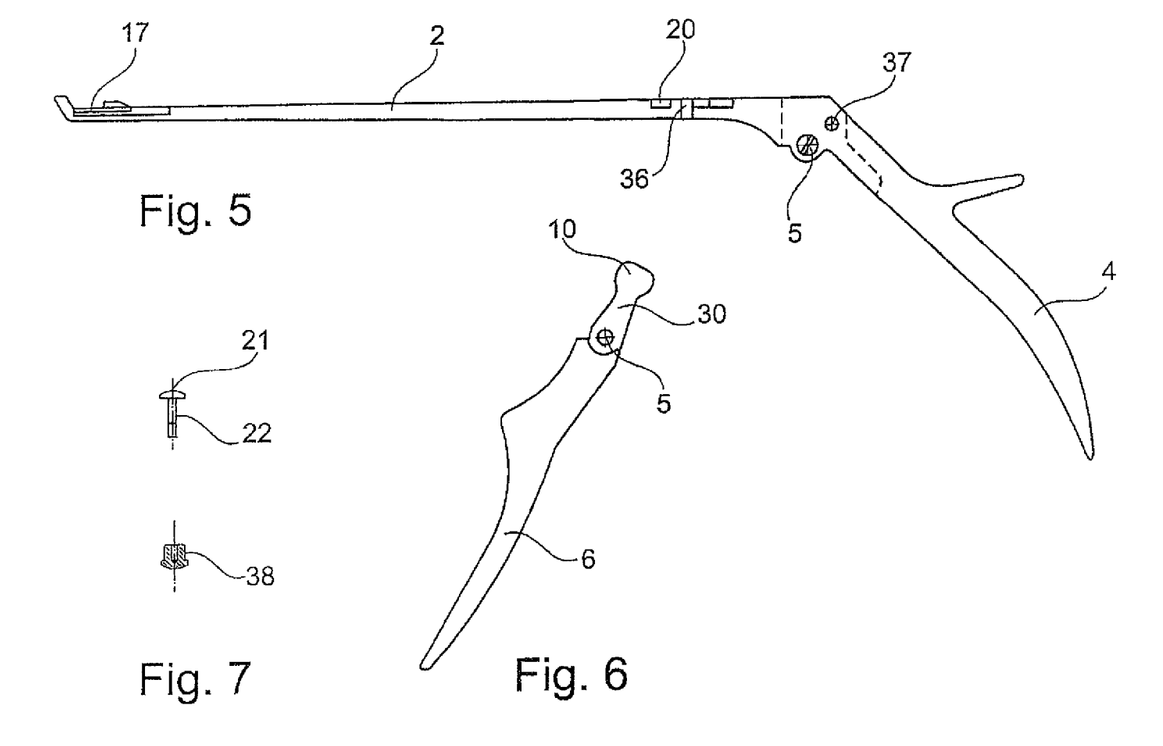
FIG. 5: a shaft of the surgical instrument with integral fixed grip part.
FIG. 6: a pivotable grip part.
FIG. 7: an exploded illustration of the rotation axis construction for the undetachable holding of the sliding part on the shaft.

FIG. 5 shows the component formed from shaft 2 and proximal grip part 4. This has the guide tracks 17, 20, already described with the aid of FIG. 1, and a through-bore 36 to receive the head screw 22 (cf. FIG. 7). In addition, a through-opening 37 can be seen, which in the assembled state is penetrated by the locking bolt 25, which is not illustrated, and the position of a pivot axis 5 for the pivotable grip part 6 illustrated in FIG. 6.

FIG. 7 shows a possibility for the undetachable mounting of the sliding part 12 on the shaft 2. The head screw 22, forming the rotation axis 21, can be seen, which is held in a counter-element 38 with internal thread. A dismantling is, indeed, theoretically possible, but not necessary. An embodiment is also able to be realized in which the component, constructed here as head screw 22, forming the rotation axis 21, is held inseparably in a counter-element, or is secured on the shaft 2 for example by caulking, with a counter-element being dispensed with.

An alternative surgical instrument 1, constructed as a conchotome, is described below with the aid of FIGS. 10*a* to 12. The conchotome is equipped with the parts or functional units shown in FIGS. 3, 6, 7, 8 and 9, which are not described again below, to avoid repetitions. Reference is to be made to the corresponding preceding text passages with regard to the mode of operation and composition of these parts.

The surgical instrument 1, constructed as a conchotome, comprises an elongated sliding part 12 which is in engagement with its distal (front) end with a jaw part 39 (acting member part), articulated pivotably on the shaft 2, of a distal jaw 40 (acting member) of the surgical instrument 1. The pivotably arranged jaw part 39, as can be seen in particular from the enlarged illustrations according to FIGS. 10*b* and 11*b*, cooperates with a further jaw part 41, which is fixed here, which is constructed in one piece with the shaft 2 of the surgical instrument 1. A rear grip part 4 (gripping arm) is likewise embodied in one piece with the shaft 2.

A distal (front) pivotable grip part 6 is pivotably arranged relative to the fixed, proximal (rear) grip part 4 about a pivot axis 5 running transversely to the longitudinal extent of the shaft 2. In the example embodiment shown, in contrast to the previously described laminectomy rongeur, no expander spring is arranged between the two grip parts 4, 6, with an embodiment of the conchotome with an expander spring basically also being able to be realized.

Except for the expander spring, the gripping and locking concept of the conchotome is identical to the gripping and locking concept of the previously described laminectomy rongeur. Thus, the (front) grip part has an upper, approximately ball-shaped end 10, which engages into a laterally open recess 11 of the sliding part 12. In this way, the sliding part 12 is longitudinally displaceable relative to the shaft 2 by means of the front, pivotable grip part 6, by pivoting thereof about the pivot axis 5.

Figure 10A:
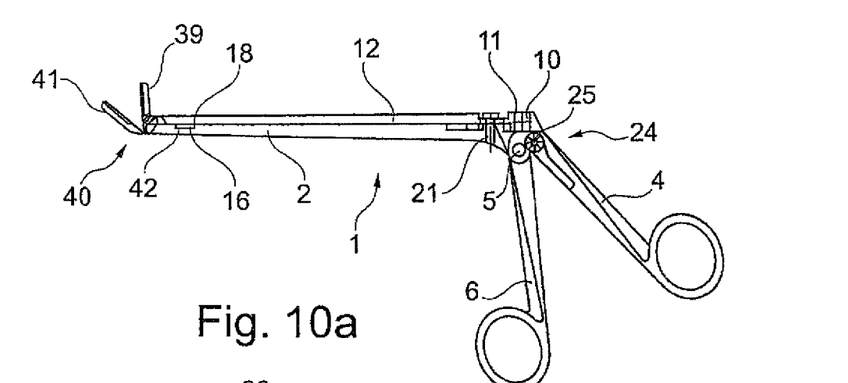
FIG. 10a: a surgical instrument, constructed as a conchotome, with opened jaw (acting member)
Figures 10B, 11A, 11B:
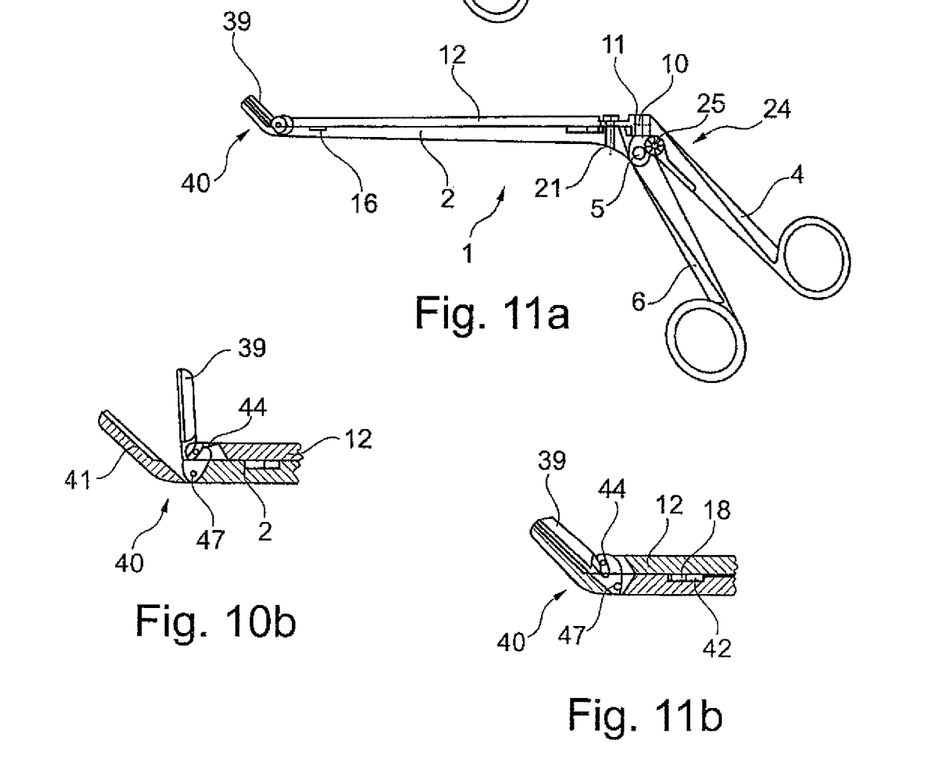

In FIGS. 10*a* to 11*b*, the sliding part 12 is shown in a working position, wherein FIG. 10*a*, 10*b* on the one hand and FIG. 11*a* and 11*b* on the other hand show axial extreme positions of the sliding part 12 within the working position. In FIGS. 10*a* and 10*b*, the sliding part 2 is shown in its proximal end positions of the working position, in which the jaw 40 is maximally opened, whereas in FIG. 11*a* and 11*b* the distal end position of the sliding part 12 is shown, in which the jaw 40 is closed, i.e. the pivotable jaw part 39 lies against the fixed jaw part 41. In the working position, the sliding part 12 is guided on the shaft with the axial displacement between the two previously mentioned maximum deflection positions. As guide 16, a T-shaped slot in cross-section (T-slot 42) is provided in the shaft 2, into which the sliding part 12 engages in the working position with a lower guide extension 18, substantially congruent in shape, T-shaped in cross-section, wherein the T shape is upside down in a view (not shown) seen from the front.

In order to make possible a facilitated cleaning of the surgical instrument 1, a rotation axis 21, extending in vertical direction, is provided for the sliding part 12. A pivoting about this rotation axis 21 is not possible in the shown working position (cf. FIGS. 10*a* to 11*b*), in which the sliding part 12 is caught in the T-slot.

Locking means 24, which secure the sliding part 12, as previously described, in its working position against an unintended transfer into the cleaning position, shown in FIG. 3 and described in detail in connection with FIG. 3, are associated with the sliding part 12. The locking means 24 and their mode of operation can be seen particularly well from a review of FIGS. 3, 8 and 9 together.

FIGS. 10*a* and 11*a* show the locking bolt 25 of the locking means 24 in its securing position. When the locking means 24 are unlocked by displacement of the locking bolt 25 contrary to the elastic force of the spring 26, a release position is displaced, the front grip part 6 lies against the second (reduced) diameter section of the locking bolt 25. In this release position (corresponding locking means 24), the stop position for the pivotable grip part 6 is displaced in a proximal direction, i.e. towards the rear, so that the sliding part, which is coupled via the upper end 10 with the pivotable grip part 6, can be displaced further towards the rear, i.e. in a proximal direction. After releasing of the sliding part 12 from the pivotably arranged jaw part 39, the sliding part can give into its cleaning position, in the plane of the drawing upwards away from the shaft 2, in which the sliding part 12 is pivotable about the rotation axis 21 for cleaning purposes. In order to make possible this springing out from the guide 16, the sliding part 12 is bent slightly upwards with its distal end before installation, therefore has a bent basic form in the unstressed state, and when it is situated in the guide 16, is pre-stressed upwards i.e. away from the shaft 2, by internal stress.

Figure 12:
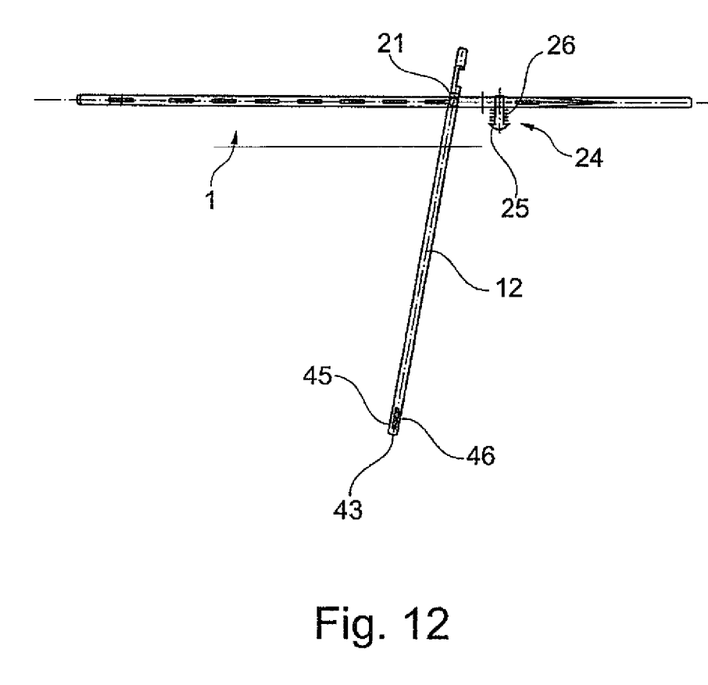

In FIGS. 10*b* and 11*b*, the jaw 40 or respectively the coupling is shown in detail between sliding part 12 and pivotable jaw part 39. It can be seen that the sliding part 12 engages with a bar-shaped carrier section running transversely to its longitudinal extent into a curved receiving slot 44, open on one side, of the jaw part 39. It can be seen that the receiving slot 44, with the jaw 40 closed, is contoured so as to be curved slightly towards the front. As can be further seen from FIGS. 10*b* and 11*b*, the receiving slot 44 is arranged at a distance from the pivot axis 47 of the jaw part 39, via which the jaw part 39 is fixed on the shaft 2. The carrier section 43, as can be seen in particular from FIG. 12, is received between two parallel, distal side sections 45, 46, therefore does not have a free end, but rather is constructed with both ends in one piece with the side sections 45, 46, or alternatively is held as a separate component on both side sections 45, 46, preferably in corresponding lateral receiving bores of the side sections 45, 46. Such an arrangement of the carrier section 43 is expedient in particular in the case of small overall sizes, in order to avoid a twisting of the sliding part 12 under load on actuation of the grip part 6. In particular in the case of larger structural shapes, one of the two side sections 45, 46 can be dispensed with, so that the carrier section 43 is only held on one side and thereby a lateral pivoting out from the receiving slot 44 is made possible. In such an embodiment, the guide 16 can be constructed for example in the manner as in the laminectomy rongeur, from which the sliding part 12 can be pivoted out laterally in the cleaning position. In the variant embodiment shown, the sliding part 12 only has to be moved away—here by pre-stressing—with its distal end upwards away from the shaft 2.

After transferring the locking means 24 into the release position (release placement), the sliding part 12 is guided out from the receiving slot 44 when the jaw part 39 is actuated manually, and can spring out upwards away from the shaft 2 owing to its pre-stressing, and can thereafter be pivoted about the rotation axis 21, as is shown in FIG. 12.

The invention claimed is:

1. Surgical instrument, with a shaft and with a one-piece sliding part longitudinally displaceable relative to the shaft, with which a grip part is associated, pivotable about a pivot axis, for longitudinal displacement, wherein the sliding part is able to be transferred from a working position, in which the sliding part is guided longitudinally displaceably on the shaft in a guide, into a cleaning position, in which the sliding part is freed from the guide and is pivotable relative to the shaft about a rotation axis oriented perpendicularly to the longitudinal extent of the shaft so that both ends of the sliding part rotate about the rotation axis, wherein the rotation axis is aligned perpendicularly to the pivot axis of the pivotable grip part, the sliding part having a laterally open recess at a proximal end of the sliding part, wherein the pivotable grip part is engaged in the laterally open recess in the working position of the sliding part and disengaged from the laterally open recess in the cleaning position, wherein the rotation axis is formed by a pin.

2. Surgical instrument according to claim 1, wherein the sliding part is secured undetachably on the shaft both in the working position and also in the cleaning position.

3. Surgical instrument according to claim 1, wherein locking means are provided, by which the sliding part is able to be secured in the working position against an unintended transfer into the cleaning position.

4. Surgical instrument according to claim 3, wherein the locking means are constructed displacing a stop position for the pivotable grip part.

5. Surgical instrument according to claim 4, wherein the locking means has a locking bolt, adjustable perpendicularly to the rotation axis, with a first diameter section defining the stop position for the pivotable grip part in the working position, and a second diameter section defining the stop position for the pivotable grip part in the cleaning position.

6. Surgical instrument according to claim 5, wherein the diameter of the first diameter section is greater than the diameter of the second diameter section.

7. Surgical instrument according to claim 5, wherein the pivotable grip part is spring-loaded against the locking bolt.

8. Surgical instrument according to claim 5, wherein the locking bolt is able to be transferred contrary to the elastic force of a spring from its securing position, in which the locking bolt secures the sliding part in its working position, into a release position, in which the sliding part is rotatable about the rotation axis and in which the stop position for the pivotable grip part is displaced with respect to the stop position for the pivotable grip part in the securing position.

9. Surgical instrument according to claim 1, wherein the shaft and sliding part cooperate in the region of their distal working ends and the sliding part is arranged actuating a jaw part.

10. Surgical instrument according to claim 9, wherein the sliding part is in engagement with the jaw part at a distance from a pivot axis of the jaw part.

11. Surgical instrument according to one claim 10, wherein the jaw part with a receiving slot, contoured obliquely or in curved form, engages behind a bar- or rod-shaped carrier section of the sliding part running transversely to the longitudinal extent of the sliding part, such that the sliding part on its longitudinal displacement pivots the jaw part about its pivot axis.

12. Surgical instrument according to claim 11, wherein the receiving slot is contoured such that the sliding part, with unlocked locking means, is displaceable in the direction of an opening of the receiving slot by manual actuation of the jaw part.

13. Surgical instrument according to claim 11, wherein the carrier section is received between two side sections of the sliding part or has a free end.

14. Surgical instrument according to claim 1, wherein the guide is constructed as a T-slot, provided in the shaft and open at the top.

15. Surgical instrument according to claim 14, wherein, in the working position, a distal section of the sliding part is pre-stressed in the direction of the longitudinal extent of the rotation axis, away from the shaft.

16. Surgical instrument according to claim 1, wherein the laterally open recess is provided so as to permit uncoupling of the sliding part by pivoting the sliding part about the rotation axis.

* * * * *